(12) United States Patent
Frenkel et al.

(10) Patent No.: US 7,102,035 B2
(45) Date of Patent: Sep. 5, 2006

(54) REMOVAL OF DIALKYL ETHERS FROM DIALKYL PEROXIDES

(75) Inventors: Peter Frenkel, Danbury, CT (US); Delphine Meeh, Longview, TX (US); Lawrence A. Bock, Longview, TX (US); Anthony Andrews, Longview, TX (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/874,906

(22) Filed: Jun. 23, 2004

(65) Prior Publication Data

US 2005/0027144 A1 Feb. 3, 2005

Related U.S. Application Data

(60) Provisional application No. 60/490,906, filed on Jul. 30, 2003.

(51) Int. Cl.
*C07C 409/00* (2006.01)
(52) U.S. Cl. .................................... 568/576
(58) Field of Classification Search ................ 568/576
See application file for complete search history.

(56) References Cited

U.S. PATENT DOCUMENTS 3,778,382 A 12/1973 Poenisch et al.
3,917,709 A 11/1975 Turner et al. ............... 260/593
4,900,850 A 2/1990 Sanderson et al. .......... 549/529
5,453,548 A 9/1995 Nedwick et al. ............ 568/576
6,225,510 B1 * 5/2001 Frenkel et al. ............. 568/558

FOREIGN PATENT DOCUMENTS

EP 0068785 A1 1/1983

OTHER PUBLICATIONS

Batt et al., Pyrolysis of Di-tertiary Butyl Peroxide, The Journal of Chemical Physics, vol. 36, No. 4, pp. 895-901, (1962).
Val'kovskii, D.G. et al., Izv. Akad. Nauk SSSR, Ser. Khim. 7:1319-27 (1963), (C.A. 59:68797).
Milas et al., Studies in Organic Peroxides, Journal of the American Chemical Society, vol. 68, pp. 205-208, (1946).
Solyanikov, V.M. et al., Izv. Akad. Nauk SSSR, Ser. Khim. 6:1400-2 (1976), (C.A. 85:123082).

* cited by examiner

*Primary Examiner*—Porfirio Nazario-Gonzalez
*Assistant Examiner*—Chukwuma Nwaonicha
(74) *Attorney, Agent, or Firm*—Daniel Reitenbach

(57) ABSTRACT

A process is disclosed for reducing the concentration of a dialkyl ether in a mixture comprising the dialkyl ether and a dialkyl peroxide wherein the process comprises treating said mixture with a strong acid.

12 Claims, No Drawings

REMOVAL OF DIALKYL ETHERS FROM DIALKYL PEROXIDES

We claim the benefit under Title 35, United States Code, § 120 to U.S. Provisional Application No. 60/490,906, filed Jul. 30, 2003, entitled REMOVAL OF DIALKYL ETHERS FROM DIALKYL PEROXIDES.

BACKGROUND OF THE INVENTION

1. Field of the Invention

The present invention relates to the reduction of impurities in dialkyl peroxides. More particularly, the present invention relates to a method for reducing the concentration of dialkyl ethers in dialkyl peroxides.

2. Description of Related Art

Methyl t-butyl ether (MTBE) is a by-product formed during the manufacture of di-t-butyl peroxide (DTBP). MTBE is a suspected threat to human health. When DTBP is used to cross-link polyethylene (PE) pipe that may be used to transport potable water, the MTBE becomes an unwanted contaminant in the pipe. The MTBE can be leached out from the pipe and render the water foul-smelling and, possibly, hazardous to human health. See Announcement of the Drinking Water Contaminant List (Mar. 2, 1998, 63 FR 10273–10287).

Two reports in the literature that state that MTBE is formed as one of the decomposition products of DTBP are Batt, L. et al., *J. Chemical Physics*, 36:895–901 (1962) and Val'kovskii, D. G. et al., *Izv. Akad. Nauk SSSR, Ser. Khim.* 7:1319–27 (1963), (C. A. 59:68797).

Two patents report general methods for the purification of DTBP:

U.S. Pat. No. 4,900,850 discloses that a tertiary butyl alcohol/ditertertiary butyl peroxide azeotrope may be recovered from a product containing tertiary butyl alcohol and ditertiary butyl peroxide by distilling the tertiary butyl alcohol product to obtain an overhead fraction containing substantially all of the ditertiary butyl peroxide as a ditertiary butyl peroxide/tertiary butyl alcohol azeotrope and other contaminants. It is also disclosed that the ditertiary butyl peroxide can be recovered from the distillate fraction by extraction with water (e.g., in a countercurrent water extraction tower) to provide a ditertiary butyl peroxide product of any desired degree of purity.

U.S. Pat. No. 5,453,548 discloses a process for the separation of ditertiary butyl peroxide from tertiary butanol that includes the step of dehydrating the tertiary butanol to isobutylene and water.

The following three references indicate the treatment of DTBP with concentrated sulfuric acid caused significant degradation of the peroxide:

U.S. Pat. No. 3,917,709 discloses that tertiary aliphatic hydroperoxides and peroxides in the presence of a highly concentrated acid catalyst are converted to a mixture of ketones and alcohols in substantially quantitative yields. The corresponding secondary aliphatic hydroperoxides yield product mixtures of alcohols, ketones and aldehydes in varying proportions, depending upon the acid concentration employed.

Milas, N. et al., *J. Am. Chem. Soc.* 68:205–208, (1946) reported that when DTBP was dissolved in concentrated sulfuric acid, a polymeric hydrocarbon slowly separated from the solution.

Solyanikov, V. M. et al., *Izv. Akad. Nauk SSSR, Ser. Khim.* 6:1400–2 (1976) (C. A. 85:123082) reported that DTBP was decomposed by hydrochloric, perchloric, and sulfuric acids. This acid-catalyzed decomposition is said to give $Me_3C+$ and $Me_3COOH$. Deprotonation of the $Me_3C+$ yields isobutene and homolysis of the $Me_3COOH$ yields free radicals.

SUMMARY OF THE INVENTION

The present invention is directed to a method for removing dialkyl ethers from dialkyl peroxides by treating the peroxides with a strong acid.

More particularly, the present invention is directed to a process for reducing the concentration of a dialkyl ether in a mixture comprising the dialkyl ether and a dialkyl peroxide comprising treating said mixture with a strong acid.

In a highly preferred embodiment, the present invention is directed to a process for reducing the concentration of methyl t-butyl ether in a mixture comprising said ether and di-t-butyl peroxide comprising treating said mixture at room temperature with sulfuric acid having an acid strength in the range of from about 10% to about 50%.

DESCRIPTION OF THE PREFERRED EMBODIMENTS

As stated above, the present invention is directed to a method for removing dialkyl ethers from dialkyl peroxides by treating the peroxides with a strong acid.

It is preferred that the strong acid be a mineral acid. Any of the common mineral acids, e.g., sulfuric, perchloric, hydrochloric, nitric, and the like, can be employed in the practice of the present invention. The most preferred mineral acid is sulfuric acid.

The alkyl groups of the dialkyl ethers that are removed by the process of the present invention can be the same or different from each other and are preferably lower alkyl groups, e.g., those having from 1 to 5 carbon atoms. Such alkyl groups include methyl, ethyl, n-propyl, isopropyl, n-butyl, isobutyl, sec-butyl, tert-butyl, 1-pentyl, 2-pentyl, 3-pentyl, 3-methylbutyl, 2-methylbutyl, and 2,2-dimethylpropyl. Preferably, the two alkyl groups of the dialkyl ether are different from one another. Most preferably, the dialkyl ether is methyl t-butyl ether.

Similarly, the alkyl groups of the dialkyl peroxides that are purified by the process of the present invention can be the same or different from each other and are preferably lower alkyl groups, e.g., those having from 1 to 5 carbon atoms, such as those specified above. It is preferred that the two alkyl groups of the dialkyl peroxide be the same. More preferably, the dialkyl peroxide is di-t-butyl peroxide.

In the practice of the present invention, the weight ratio of the strong acid to the dialkyl peroxide being purified can range from about 10:1 to about 1:10. Preferably, the ratio will be in the range of from about 2:1 to about 1:2. A ratio of about 1:1 is most preferred.

The strong acid can be concentrated or dilute. In a preferred embodiment, the acid concentration can range from about 10% to about 65%. A more preferred concentration range is from about 10% to about 50%. Where sulfuric acid is employed as the strong acid, the most preferred concentration is about 50%.

The reaction conditions, i.e., temperature and pressure, under which the purification reaction of the present invention is carried out, are not critical, but it is preferred that they be relatively mild. More preferably, the reaction is carried out under ambient conditions, i.e., room temperature and atmospheric pressure.

Thus, when DTBP was treated with an equal weight of 10 to 50% sulfuric acid for several hours at ambient temperature, the MTBE concentration fell from an initial level of 72 ppm to less than 1 ppm, depending on the strength of the acid. These results are shown in the examples below. When the experiments were repeated at 50° C., the levels of residual MTBE were actually higher than what was found at ambient temperature, probably because of a small amount of decomposition of the DTBP at the higher temperature.

The advantages and the important features of the present invention will be more apparent from the following examples.

EXAMPLES

Example 1

Three hundred grams of DTBP containing 72 ppm of methyl t-butyl ether was placed in a flask and stirred with 300 grams of 35% sulfuric acid for two hours at room temperature. After the stirring time was completed, the mixture was allowed to separate and the aqueous phase was discarded. The organic layer was washed three times with an equal volume of water to remove any residual acid. Analysis by gas chromatography showed an MTBE content of 5.5 ppm. The gas chromatographic analysis was performed using a Hewlett Packard 5890 G.C. with an HP-1 dimethylpolysiloxane column, 30 meters by 0.53 mm by 3.0 micron film thickness. The injector temperature was 120° C. The temperature program was 40° C. for five minutes, then ramped to 80° C. at 10° C. per minute and held for six minutes. 2-Butanol was used as the internal standard. The result of the experiment is shown in Table 1.

Example 2

Example 1 was repeated except that 10% sulfuric acid was used as the acid, rather than the 35% acid that was employed therein. The result is shown in Table 1.

Example 3

Example 1 was repeated except that 50% sulfuric acid was used as the acid, rather than the 35% acid that was employed therein. The result is shown in Table 1.

TABLE 1

Experimental Results
Each experiment was conducted for two hours at 25° C.
Crude products were washed three times with equal volumes of water.

| Example | Acid Strength Used for Wash | MTBE content (ppm) |
|---|---|---|
| — | Starting DTBP | 72 |
| 2 | 10% Sulfuric | 21 |
| 1 | 35% Sulfuric | 5.5 |
| 3 | 50% Sulfuric | <1 |

Example 4

Fifty grams of DTBP containing 38 ppm of methyl t-butyl ether was placed in a flask and stirred with 50 grams of 35% perchloric acid for two hours at room temperature. After the stirring time was completed, the mixture was treated as described in Example 1 above. Gas chromatographic analysis showed the presence of 11 ppm of MTBE.

Example 5

Example 4 was repeated except that the stirring time was three hours. Analysis of the recovered DTBP showed the presence of 7 ppm of MTBE.

In view of the many changes and modifications that can be made without departing from principles underlying the invention, reference should be made to the appended claims for an understanding of the scope of the protection to be afforded the invention.

What is claimed is:

1. A process for reducing the concentration of a dialkyl ether in a mixture comprising the dialkyl ether and a dialkyl peroxide comprising treating said mixture with a strong acid.

2. The process of claim 1 wherein the strong acid is a mineral acid.

3. The process of claim 2 wherein the mineral acid is selected from the group consisting of sulfuric acid, perchloric acid, hydrochloric acid, and nitric acid.

4. The process of claim 3 wherein the acid is sulfuric acid.

5. The process of claim 4 wherein the acid strength of the sulfuric acid is in the range of from about 10% to about 50%.

6. The process of claim 1 wherein the weight ratio of the strong acid to the dialkyl peroxide being purified is in the range from about 10:1 to about 1:10.

7. The process of claim 1 wherein the treatment is carried out at a temperature less than or equal to about 50° C.

8. The process of claim 7 wherein the treatment is carried out at room temperature.

9. The process of claim 1 wherein the two alkyl groups of the dialkyl ether are independently selected from those having from one to five carbon atoms.

10. The process of claim 1 wherein the two alkyl groups of the dialkyl peroxide are independently selected from those having from one to five carbon atoms.

11. The process of claim 1 wherein the dialkyl ether is methyl t-butyl ether and the dialkyl peroxide is di-t-butyl peroxide.

12. A process for reducing the concentration of methyl t-butyl ether in a mixture comprising said ether and di-t-butyl peroxide comprising treating said mixture at room temperature with sulfuric acid having an acid strength in the range of from about 10% to about 50%.

* * * * *